United States Patent
Warm (10) Patent No.: US 9,393,157 B2
(45) Date of Patent: Jul. 19, 2016

(54) IMAGE PROCESSING METHOD FOR DETERMINING FOCUS DEPTH OF A REFRACTIVE LASER

(75) Inventor: Berndt Warm, Schwaig (DE)

(73) Assignee: WAVELIGHT GMBH, Erlangen (DE)

( * ) Notice: Subject to any disclaimer, the term of this patent is extended or adjusted under 35 U.S.C. 154(b) by 225 days.

(21) Appl. No.: 14/366,654

(22) PCT Filed: Dec. 29, 2011

(86) PCT No.: PCT/EP2011/006605
§ 371 (c)(1),
(2), (4) Date: Oct. 22, 2014

(87) PCT Pub. No.: WO2013/097881
PCT Pub. Date: Jul. 4, 2013

(65) Prior Publication Data
US 2015/0036899 A1 Feb. 5, 2015

(51) Int. Cl.
 *G06K 9/00* (2006.01)
 *A61F 9/008* (2006.01)
 *G06T 7/00* (2006.01)

(52) U.S. Cl.
 CPC ........... *A61F 9/00825* (2013.01); *G06T 7/0057* (2013.01); *A61F 2009/00844* (2013.01); *A61F 2009/00855* (2013.01)

(58) Field of Classification Search
CPC combination set(s) only.
See application file for complete search history.

(56) References Cited

U.S. PATENT DOCUMENTS

| | | | |
|---|---|---|---|
| 4,826,285 | A | 5/1989 | Horner |
| 7,982,169 | B2 | 7/2011 | Kittelmann et al. |
| 8,852,176 | B2 | 10/2014 | Riedel et al. |
| 2004/0070761 | A1 | 4/2004 | Horvath |
| 2009/0127429 | A1 | 5/2009 | Kittelmann et al. |
| 2010/0324542 | A1 | 12/2010 | Kurtz |

FOREIGN PATENT DOCUMENTS

| | | |
|---|---|---|
| CN | 101389296 A1 | 3/2009 |
| DE | 102006007750 A1 | 8/2007 |
| JP | H8016785 A | 1/1996 |
| JP | 2006502410 | 1/2006 |
| JP | 2009527265 | 7/2009 |
| KR | 1020050051690 | 6/2005 |
| KR | 1020080108474 | 12/2008 |

(Continued)

OTHER PUBLICATIONS

CN201180076101.1; English Translation of Feb. 28, 2015 CN Office Action citing Jianhao et al., 143-145.

(Continued)

*Primary Examiner* — Duy M Dang
(74) *Attorney, Agent, or Firm* — Jason Finch (57) ABSTRACT

The present invention relates to a laser apparatus, system, and method for determining a depth of a focus point of a laser beam. An interface device is coupleable to the laser apparatus and has an applanation element comprising a front surface and a back surface. A laser beam having a predefined shape is focussed through the applanation element at a focus point. A superimposed image of a spurious reflection, which is reflected from the front surface of the applanation element, with a standard reflection, which is reflected from the back surface of the applanation element, is detected. The spurious reflection is then filtered out of the superimposed image. Based on the remaining standard reflection, the depth of the focus point of the laser beam can be determined.

13 Claims, 5 Drawing Sheets

(56) References Cited

FOREIGN PATENT DOCUMENTS

| RU | 2166304 C1 | 5/2001 |
| WO | 2004032810 A2 | 4/2004 |
| WO | 2007096136 A1 | 8/2007 |
| WO | 2010000279 A1 | 1/2010 |

OTHER PUBLICATIONS

Jianhao et al., 143-145, Material from CN Textbook: Principle of Soft Computing and It's Application in Engineering, Sep. 2011, 3 pgs.
Du Shu-Song, et. al., Stray light analysis of Fabry-Parot interference imaging spectrometer, 246-251, Journal of Applied Optics, vol. 30, No. 2, Mar. 2009, China [including English translation of relevant portion: Left column of second page (p. 247 of the journal].

IMAGE PROCESSING METHOD FOR DETERMINING FOCUS DEPTH OF A REFRACTIVE LASER

CROSS REFERENCE TO RELATED APPLICATIONS

This application is a section 371 national stage phase of International Application No. PCT/EP2011/006605, filed 29 Dec. 2011, titled "IMAGE PROCESSING METHOD FOR DETERMINING FOCUS DEPTH OF A REFRACTIVE LASER," which is hereby incorporated by reference in its entirety.

BACKGROUND

For material processing lasers, and in particular lasers used in ophthalmological surgery, it is essential to determine the depth of the focus of the laser beam exactly, so as to achieve a high-quality and precise cut.

Refractive lasers are a particular kind of material processing laser which are used in LASIK (laser assisted in-situ keratomileusis) surgery. LASIK surgery is performed in three steps. A first step is to create a flap of corneal tissue. A second step is reshaping or remodelling of the cornea underneath the flap with the refractive laser. In a final step, the flap is repositioned.

The human cornea consists of five layers. The outer layer is the epithelium, a thin tissue layer of fast-growing and easily regenerated cells, typically composed of about six layers of cells. Next, the Bowman's layer, which is 8-14 µm thick, is a condensed layer of collagen that protects the stroma. The stroma is a transparent middle layer, consisting of regularly arranged collagen fibers, along with sparsely distributed interconnected keratocytes, which are cells responsible for general repair and maintenance. The Descemet's membrane is a thin acellular layer around 5-20 µm thick. Finally, the endothelium is a layer, approximately 5 µm thick, of mitochondria-rich cells.

The stroma is the thickest layer of the cornea, accounting for up to 90% of the corneal thickness. A remodeling or reshaping of the stroma during surgery alters the light-focussing capability of the cornea, which results in a correction to the patient's vision.

During LASIK surgery, to control the depth of the focus of the laser beam more exactly, a flat or curved transparent or/and translucent plane is placed in contact with the outer surface of the eye. This plane is also called an applanation element. The applanation element has a front surface which is typically coated with a reflex-minimizing layer, and a back surface which is in contact with the eye.

When cutting the flap, the depth of the focus of the laser must be controlled very precisely. The flap is cut to a depth of approximately 80 µm to 500 µm, such as approximately 120 µm. The flap is typically created very near the Bowman's layer to avoid trauma caused by pulling back the flap but sufficiently far from the Bowman's layer to avoid breaching the layer. To enable consistent, high-quality results, the focus depth of the laser beam must be controllable to within a precision of a few micrometers.

In current LASIK surgery systems, the depth of the focus of the laser, relative to the cornea surface of the eye, is calibrated (or recalibrated) before the start of each surgery.

To determine the exact depth of the focus of the laser beam during calibration, the back surface of an applanation element is in contact with the eye, and a laser beam having a particular pattern is directed at the eye. The exact depth of the focus of the laser beam relative to the back surface of the applanation element is calculated based on the measured pattern of light reflected from the back surface of the applanation element. To ensure that there are no spurious reflections from other surfaces which would compromise the quality of the calculations, the front surface of the applanation element is coated with a high-transmissivity reflection-minimizing coating.

PROBLEM STATEMENT

However, such a high-transmissivity coating is quite expensive, and therefore it would be desirable to find a method for determining the exact depth of the focus of the laser beam which functions even when the front surface of the applanation element is not coated with a reflection-minimizing highly transmissive layer. This problem is solved by the subject matter of the independent claims. Advantageous embodiments are defined by the dependent claims.

SUMMARY OF THE INVENTION

A first aspect of an ophthalmological laser apparatus is described according to claim 1. An interface device is coupleable to the laser apparatus and has an applanation element that may be transparent or/and translucent to a laser beam produced by the laser apparatus. The applanation element has a front surface and a back surface. The laser apparatus comprises optics that are adapted to focus the laser beam, which has a predefined shape, through the applanation element at a focus point. Furthermore, the laser apparatus comprises a detection element that is adapted to detect a superimposed image of a spurious reflection, which is reflected from the front surface, with a standard reflection, which is reflected from the back surface. The laser apparatus also comprises a processor that is adapted to numerically filter out the spurious reflection from the superimposed image, and determine a depth of the focus point of the laser beam based on the remaining standard reflection.

The ophthalmological laser apparatus according to the first aspect allows the depth of the focus of the laser beam to be determined exactly, even when the front surface of the applanation element is free from a reflection-minimizing coating.

In one embodiment according to the first aspect, the ophthalmological laser apparatus may further comprise a mask for covering at least a portion of the laser beam. In this case, the optics may be adapted to focus the laser beam through the mask so as to produce the predefined shape. According to this embodiment, a suitable mask may be selected which is adapted to provide exact results for determining the depth of the focus of the laser beam.

In a further embodiment according to the first aspect, the processor for filtering the spurious reflection may be adapted to convolute the superimposed image with a predefined reference pattern to produce an auxiliary image. The processor may be adapted to next evaluate the auxiliary image to identify a maximum point having a highest intensity. Finally, the processor may be adapted to reposition the reference pattern based on a location of the maximum point, and multiply the superimposed image with the repositioned reference pattern to produce the standard reflection. According to this embodiment, the center-point of a standard reflection can be determined, and based on this information, a spurious reflection can be eliminated.

In a refinement of the previous embodiment, the reference pattern may comprise a centre point, and the processor may be adapted to reposition the reference pattern such that the centre point and the location of the maximum point are superimposed. According to this embodiment, points in which a standard reflection may be located can be identified, thus ensuring that none of the standard reflection is cancelled when the spurious reflection is eliminated.

Additionally or alternatively, the convolution of the superimposed image with the reference pattern may be performed as a multiplication in the frequency domain. In a refinement of this embodiment, the processor may be adapted to apply a Fourier-transform to the superimposed image. The processor may then be adapted to multiply the Fourier-transformed superimposed image with a Fourier-transform of the reference pattern to produce a transformed auxiliary image. Finally, the processor may be adapted to perform a reverse-Fourier-transform on the transformed auxiliary image to produce the auxiliary image. This allows the calculation of the convoluted superimposed image to be performed more quickly, as performing a convolution in the spatial domain can be very computationally expensive.

In a further embodiment of the first aspect, the applanation element may be free from a reflection-minimizing coating.

In either of the previous two embodiments, the back surface of the applanation element may be adapted to lie in contact to the eye that is to be examined. This allows the distance between the optics and the surface of the eye to be held constant over the course of a determination procedure, thus ensuring that the depth of focus is measured correctly throughout.

A second aspect is a laser system with the laser apparatus according to the first aspect or one of the embodiments of the first aspect. The laser system further comprises an interface device which is coupleable to the laser apparatus and has an applanation element which is transparent and/or translucent to a laser beam produced by the laser apparatus. The applanation element comprises a front surface and a back surface.

A third aspect is a method to determine a depth of a focus point of a laser beam provided by the laser apparatus as described herein. In a first step of this method, a laser beam, which has a predefined shape, is focused through an applanation element at a focus. The applanation element has a front surface and a back surface. The applanation element may be a transparent and/or translucent applanation element, i.e. it may be transparent and/or translucent to the laser beam. In a second step, a superimposed image is detected. The superimposed image consists of a spurious reflection, which is reflected from the front surface, superimposed with a standard reflection, which is reflected from the back surface. In a third step, the spurious reflection is numerically filtered out from the superimposed image. In a final step, a depth of the focus point of the laser beam is determined based on the remaining standard reflection.

The method according to the third aspect allows the depth of the focus of the laser beam to be determined exactly, even when the front surface of the applanation element is free from a reflection-minimizing coating.

In an embodiment according to the third aspect, the step of filtering out the spurious reflection may comprise: convoluting the superimposed image with a predefined reference pattern, to produce an auxiliary image; evaluating the auxiliary image, to identify a maximum point having a highest intensity; repositioning the reference pattern based on a location of the maximum point; and multiplying the superimposed image with the repositioned reference pattern, to produce the standard reflection. According to this embodiment, the center-point of a standard reflection can be determined, and based on this information, a spurious reflection can be eliminated.

According to this embodiment, the step of convoluting may comprise: applying a Fourier-transform to the superimposed image; multiplying the Fourier-transformed superimposed image with a Fourier-transform of the reference pattern, to produce a transformed auxiliary image; and performing a reverse-Fourier-transform on the transformed auxiliary image to produce the auxiliary image. This allows the calculation of the convoluted superimposed image to be performed more quickly, as performing a convolution in the spatial domain can be very computationally expensive.

A fourth aspect is a computer program with program code portions, that, when loaded onto a computer or processor, or when running on a computer or processor, causes the computer or processor to execute any of the method aspects described herein.

The computer program may be stored on a program storage device or computer program product.

In the above, the operation "Fourier transform" refers to any discrete Fourier transform, such as the Fast Fourier Transform (FFT). However, any computational method suitable for transforming a spatial signal into the frequency domain may be used in places where "Fourier transform" is referred to.

The laser apparatus, the laser system, the corresponding method and computer program are described herein with respect to ophthalmology. It is, however, also conceivable that the laser apparatus, the laser system, the corresponding method and computer program are used in different technical fields like dermatology or material processing.

BRIEF DESCRIPTION OF THE DRAWINGS

The invention will be explained further on the basis of the appended Figures, which are schematic throughout.

DETAILED DESCRIPTION

Figure 1:
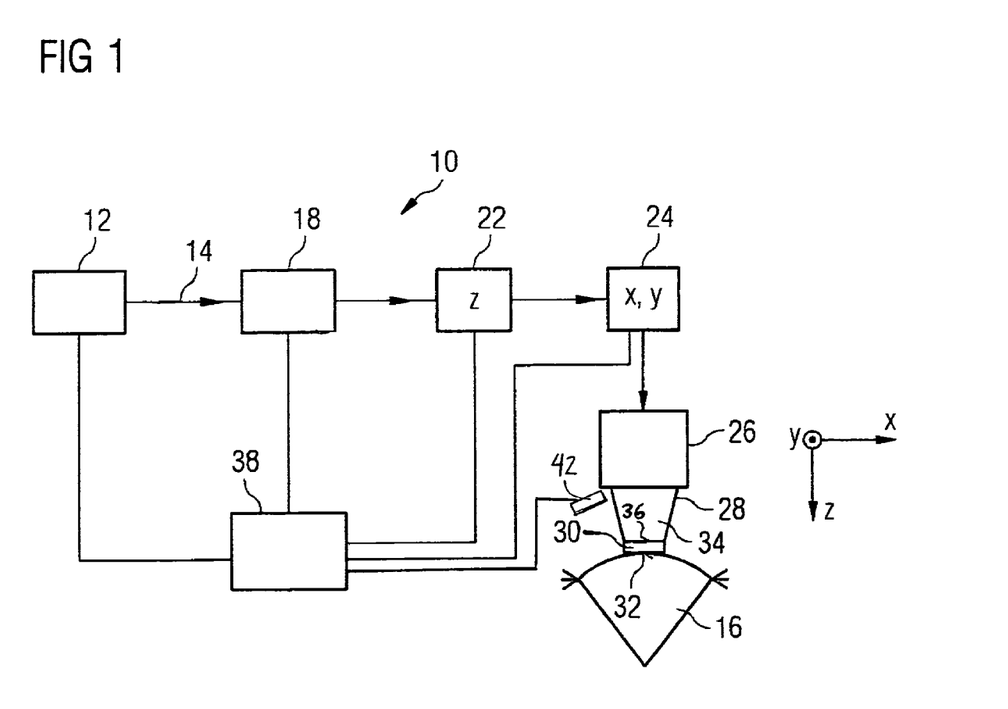
FIG. 1 shows a schematic diagram of a system comprising a laser apparatus according to one embodiment of the present invention.

FIG. 1 shows a laser system 10 for focusing a laser beam 14 at a focus point within an eye 16.

The laser system comprises a laser source 12. The laser source 12 may include, for example, a laser oscillator (e.g. solid-state laser oscillator), a pre-amplifier, which increases the pulse power of the laser pulses emitted from the oscillator and simultaneously temporally stretches them, a subsequent pulse-picker, which selects individual laser pulses from the pre-amplified laser pulses of the oscillator, in order to lower the repetition rate to a desired degree, a power amplifier, which amplifies the selected, still temporally stretched, pulses to the pulse energy needed for the application, and a pulse compressor, which temporally compresses the pulses output from the power amplifier to the pulse duration desired for the application.

The laser source 12 generates a pulsed laser beam 14. The pulse duration of the radiation pulses is chosen to either generate reflected light signals, for diagnostic purposes, or for creating incisions in the corneal tissue of an eye 16 of a patient to be treated. The radiation pulses of the laser beam 14 have a pulse duration in the nanosecond, picosecond, femtosecond or attosecond range.

The laser beam 14 generated by the laser source 12 furthermore has a pulse repetition rate such as is desired for the application in question. The repetition rate of the radiation pulses emitted from the laser device 10 and directed onto the eye 16 corresponds to the repetition rate of the radiation pulses that are generated at the output of the laser source 12. Alternatively, if required by a predetermined machining profile for the eye 16, a portion of the radiation pulses emitted from the laser source 12 are blanked by means of an optical switch 18 arranged in the radiation path of the laser beam 14. Such blanked radiation pulses accordingly do not reach the eye 16.

The optical switch 18, which is also called a pulse modulator, may, for example, take the form of an acousto-optical modulator or an electro-optical modulator. Generally, the optical switch 18 may contain arbitrary optically active elements that enable a rapid blanking of individual laser pulses. The optical switch 18 may, for example, contain a beam trap, which serves to absorb radiation pulses to be blanked. The optical switch 18 can deflect such radiation pulses to be blanked from the normal beam path of the radiation pulses of the laser beam 14 and direct them onto the beam trap.

Further optical components which are arranged in the beam path of the laser beam 14 include a z-controller 22 and an x-y controller 24. The z-controller 22 controls the longitudinal location of the focal point of the laser beam 14; the x-y controller 24, on the other hand, controls the transverse location of the focal point. A coordinate frame that represents the x-y-z directions in the region of the eye 16 has been drawn in FIG. 1 for the purpose of illustration. In this context, the term 'longitudinal' refers to the direction of beam propagation, which conventionally is designated as the z-direction. Similarly, 'transverse' refers to a direction transverse to the direction of propagation of the laser beam 14, which conventionally is designated as the x-y plane.

To achieve a transverse deflection of the laser beam 14, the x-y controller 24 may, for example, include a pair of galvanometric actuated scanner mirrors that are capable of tilting about mutually perpendicular axes. The z-controller 22 may, for example, contain a longitudinally adjustable lens or a lens of variable refractive power or a deformable mirror, with which the divergence of the laser beam 14, and consequently the z-position of the beam focus, can be controlled. Such an adjustable lens or mirror may be contained in a beam expander which expands the laser beam 14 emitted from the laser source 12. The beam expander may, for example, be configured as a Galilean telescope.

The laser apparatus of the first embodiment comprises a focusing objective, also referred to as optics 26, arranged in the beam path of the laser beam 14. The optics 26 serve to focus the laser beam 14 onto a desired location on or in the eye 16, in particular within the cornea. The focusing optics 26 may be an f-theta objective.

The optical switch 18, the z-controller 22, the x-y controller 24 and the focusing objective 26 do not have to be arranged in the order represented in FIG. 1. For example, the optical switch 18 may, without loss of generality, be arranged in the beam path downstream of the z-controller 22. If desired, the x-y controller 24 and z-controller 22 may be combined to form a single structural unit. The order and grouping of the components shown in FIG. 1 is in no way to be understood as restrictive.

On the beam-exit side of the focusing objective 26, an applanation element 30 constitutes an abutment interface for the cornea of the eye 16. The applanation element 30 is transparent or/and at least translucent to the laser radiation. On its back surface 32, facing towards the eye, the applanation element 30 includes an abutment face for the cornea of the eye 16. On its upper side, opposite the surface of the eye, the applanation element 30 includes a front surface 36, which is free of any reflection-minimizing coating. In the exemplary case shown, the back surface 32 is realised as a plane surface. The back surface 32 levels the cornea when the applanation element 30 is placed in contact with the eye 16 with appropriate pressure or when the cornea is aspirated onto the back surface 32 by underpressure. As shown in FIG. 1, the eye 16 is bearing against the planar back surface 32 of the applanation element 30.

The applanation element 30, which in the case of plane-parallel design is ordinarily is designated as the applanation plate, is fitted to the narrower end of a conically widening carrier sleeve 34. The connection between the applanation element 30 and the carrier sleeve 34 may be permanent, for example by virtue of adhesion bonding, or it may be detachable, for instance by virtue of a screw coupling. It is also conceivable to use a single optical injection-moulded part which functions as both the carrier sleeve 34 and the applanation element 30. In a manner not represented in detail, the carrier sleeve 34 has coupling structures at its wider sleeve end, which in the drawing is the upper end. The coupling structures are suitable for coupling the carrier sleeve 34 onto the focusing objective 26.

The laser system 10 also comprises a detection element 42, such as a camera, which is adapted to collect images and transfer said images to the control computer 38.

The laser source 12, the optical switch 18, the detection element 42, and the two scanners 22, 24, are controlled by a control computer 38 which operates in accordance with a control program stored in a memory. The control program contains instructions (program code) that are executed by the control computer 38 so as to determine and control the location of the beam focus of the laser beam 14 in the cornea, in the lens or at another location of the eye 16 bearing against the contact element 30.

The laser system 10 may also comprise an interface module (not shown) connected to control computer 38, to allow a user to input commands to the control computer 38. The interface module may comprise a screen or monitor to enable the user to view status information about components of the laser system 10, and/or to view the data collected by the detection element 42.

Figure 2:
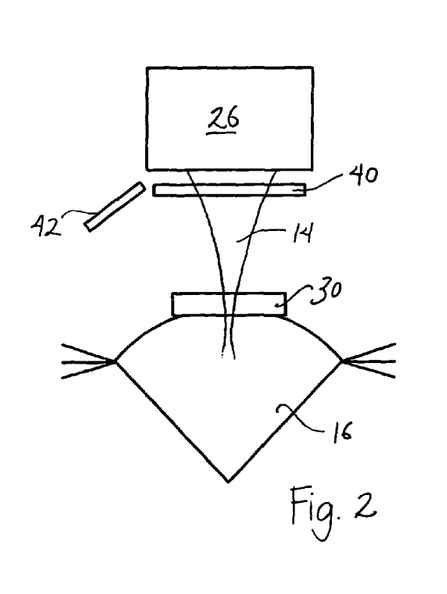
FIG. 2 shows a schematic diagram of a portion of the laser apparatus according to the embodiment of FIG. 1.

In FIG. 2, the portion of laser system 10 which forms the laser apparatus is shown in more detail. In the path of the laser beam 14 between the focusing objective 26 and the applanation element 30, a mask 40 is provided. The mask 40 is formed of a material which is opaque to the light of the laser beam 14. The mask 40 is dimensioned so as to cover substantially the entire laser beam 14. A square mask 40 is shown, but other convex shapes are possible, such as a regular or irregular polygon or a circle.

Figure 3:
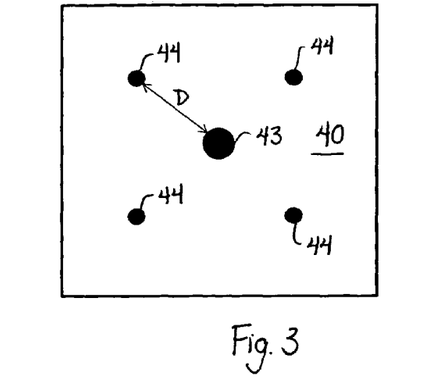
FIG. 3 shows a plan view of a mask used in the embodiment according to FIG. 2.

A plan view of the mask 40 is shown in FIG. 3. The mask 40 has a center opening 43 and one or more outer openings 44, the openings 43, 44 being adapted to let light from the laser beam 14 pass through. The outer openings 44 are each spaced at an equal distance D from the center opening 43. The distance D is less than half of the diameter of the laser beam 14, such that light from the outer edge of the laser beam 14 passes through the outer openings 44. The outer openings 44 may be distributed evenly about an imagined circumference centered at the center opening 43, but uneven distributions of the outer openings 44 about the imagined circumference are also possible.

Figure 4:
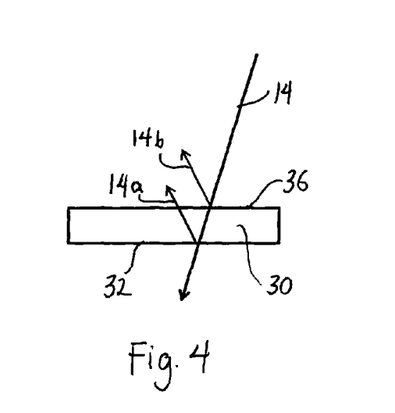
FIG. 4 shows a schematic diagram of light passing through an applanation element according to the embodiment of FIG. 1.

FIG. 4 illustrates the transmissive/reflective properties of the applanation element 30 when a beam of light 14 is directed toward it. When the light reaches the front surface 36 of the applanation element 30, most of the light continues in the same direction but a portion of the light is reflected back, forming a spurious reflection 14b.

The known art provides for a reflection-minimizing coating on the front surface 36 of the applanation element 30, so as to suppress the spurious reflection 14b. However, in the present embodiment, the front surface 36 is free from a reflection-minimizing coating, and therefore light incident on the front surface 36 results in a spurious reflection 14b.

The remaining light in the laser beam 14 then passes through the applanation element 30, and reaches the back surface 32 of the applanation element. Here again, a portion of the light is reflected back, forming a standard reflection 14a.

The reflected light from the standard reflection 14a and spurious reflection 14b is collected by the detection element 42 in the form of an output image.

In known systems, due to the provision of a reflection-minimizing coating on the back surface 36, the output image consisted of only a standard reflection 14a. If using the mask 40 shown in FIG. 3, a reflection similar to the image shown in FIG. 6 would be produced, consisting of a central bright point representing the standard reflection 14a of light which passed through the center opening 43, and four outer bright points, representing the standard reflections 14a of light which passed through the outer openings 44. Based on the distance between the central point and the outer points, the depth of the focus of the laser beam 14 can be calculated.

Figure 7:
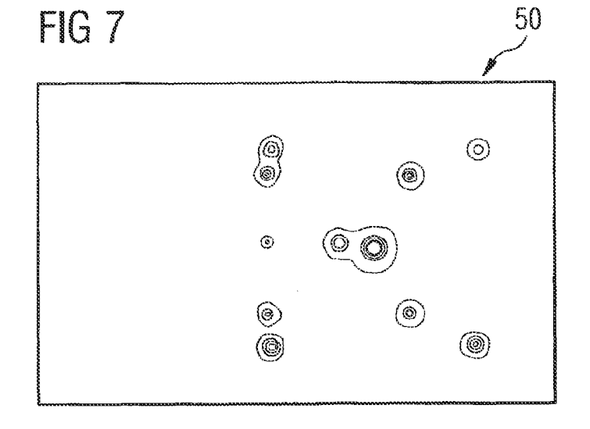
FIG. 7 shows an image consisting of a spurious reflection superimposed with a standard reflection in accordance with the embodiment of FIG. 5.

In the present embodiment, a reflection as shown in FIG. 7 is produced when using the mask 40 shown in FIG. 3. The image consists of a standard reflection 14a superimposed with a spurious reflection 14b. The points in the spurious reflection 14b have a similar configuration to the points in the standard reflection 14a, the configuration being determined by the openings 43, 44 of the mask 40. However, the points in the spurious reflection 14b have a lower intensity than the points in the standard reflection 14a. The points of the spurious reflection 14b are furthermore more widely dispersed than the points of the standard reflection 14a. Finally, the spurious reflection 14b may be incomplete, with only some of the outer points registering in the image.

In order to calculate the depth of the focus of the laser beam 14, the superimposed image of FIG. 7 must therefore be filtered, and the spurious reflection 14b removed, such that the depth of the focus of the laser beam 14 can be calculated based on the standard reflection 14a.

Figure 5:
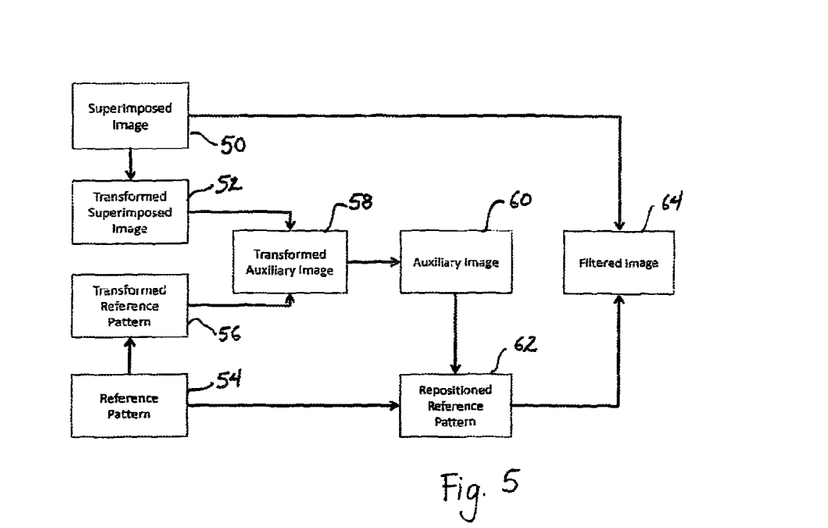
FIG. 5 shows a block diagram of the calculation steps of a method according to an embodiment of the invention.

FIG. 5 illustrates the steps for filtering the superimposed image, such as the image shown in FIG. 7, in accordance with one embodiment.

Figure 8:
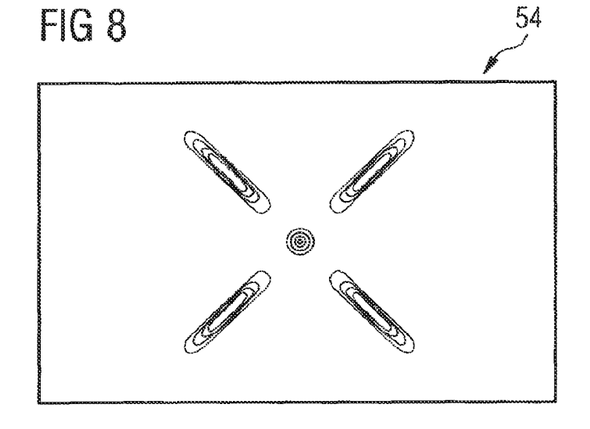
FIG. 8 shows a reference pattern in accordance with the embodiment of FIG. 5.
Figure 9:
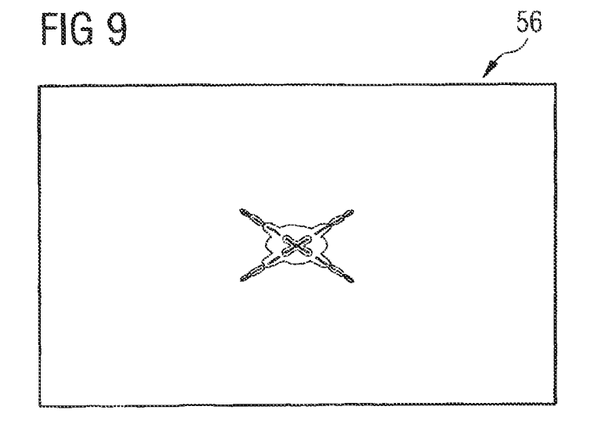
FIG. 9 shows the Fourier transformation of the reference pattern of FIG. 8.

In a first step, a reference pattern 54 is determined based on the pattern of the mask 40. As shown in FIG. 8, the reference pattern 54 consists of a superposition of the locations of the points produced at all possible focus depths of the laser beam 14, as part of the standard reflection 14a of a particular mask 40. A Fourier-transform is performed on the reference pattern 54 to produce a transformed reference pattern 56, as shown in FIG. 9.

The determination of the reference pattern 54 and calculation of the transformed reference pattern 56 may be performed only once, before the system 10 is put into use, and the transformed reference pattern 56 may be stored in a memory of the control computer 38. In this way, these operations do not have to be repeated during each filtering operation; instead, the transformed reference pattern 56 corresponding to mask 40 may simply be retrieved from memory.

The operations of the first step may be performed by the control computer 38, or they may be performed on an external processor, and the results loaded into the memory of the control computer 38. The remaining steps are performed by the control computer 38.

In a second step which may be performed before, after, or in parallel to the first step, the superimposed image 50 shown in FIG. 7 is Fourier-transformed to produce a transformed superimposed image 52.

Figure 10:
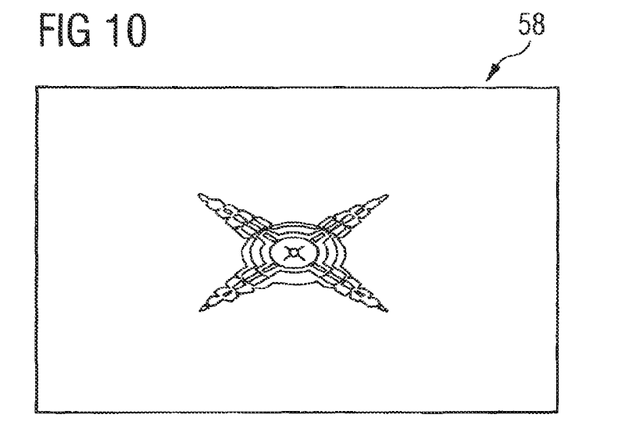
FIG. 10 shows the result of multiplying the Fourier-transformed reference pattern of FIG. 9 with a Fourier transformation of the superimposed image of FIG. 7.

In a third step, the transformed superimposed image 52 is multiplied with the transformed reference pattern 56 to produce a transformed auxiliary image 58, as shown in FIG. 10.

Figure 11:
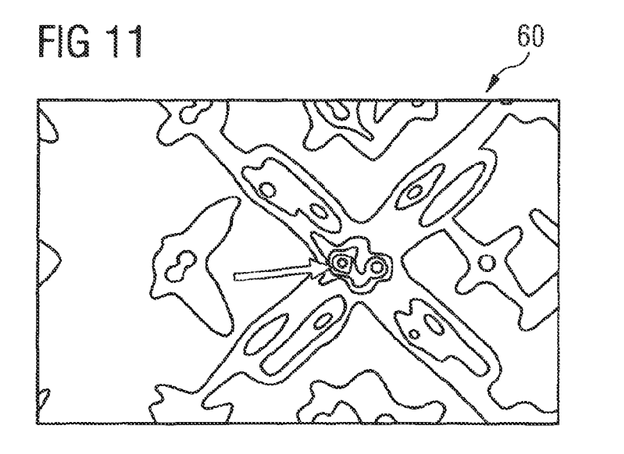
FIG. 11 shows a reverse Fourier transform of the image of FIG. 10.

In a fourth step, the transformed auxiliary image 58 is subjected to a reverse-Fourier-transform, to produce a further auxiliary image 60, as shown in FIG. 11. The auxiliary image 60 represents a convolution of the superimposed image 50 with the reference pattern 54.

In a fifth step, the auxiliary image 60 is scanned to identify a highest-intensity point, indicated by an arrow in FIG. 11. The highest-intensity point is the brightest point in the auxiliary image 60, and corresponds to the location of a center of the standard reflection 14a.

In a sixth step, the reference pattern 54 from FIG. 8 is repositioned, such that the center point of the reference pattern 54 coincides with the location of the highest-intensity point identified in the auxiliary image 60 from FIG. 11. The repositioned reference pattern 62 is shown in FIG. 12.

Figure 6:
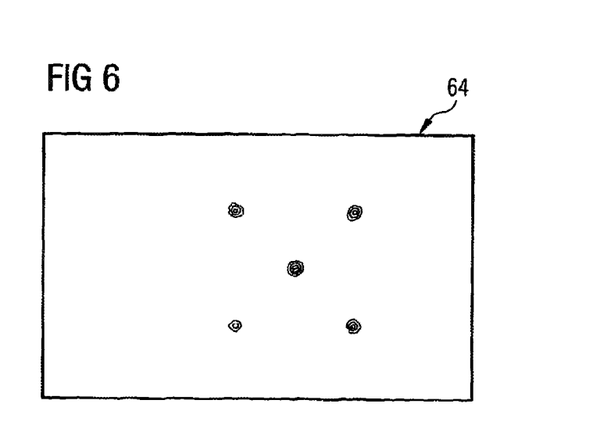
FIG. 6 shows a filtered image suitable for calculating the depth of focus of a laser beam.
Figure 12:
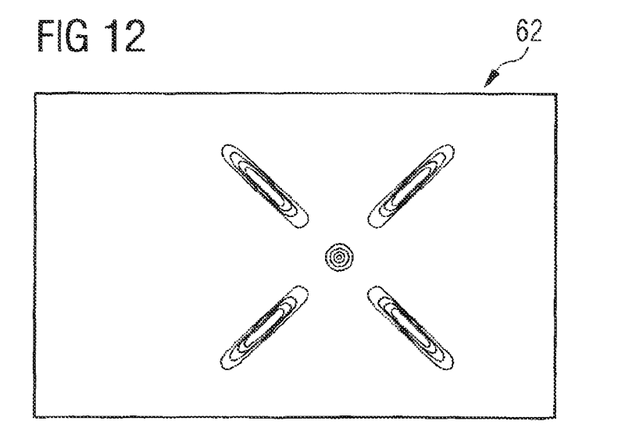
FIG. 12 shows a repositioned reference pattern in accordance with the embodiment of FIG. 5.

Finally, in a seventh step, the superimposed image 50 from FIG. 7 is multiplied with the repositioned reference pattern 62 from FIG. 12, to produce a filtered image 64, as shown in FIG. 6. The filtered image 64 is essentially identical to the standard reflection 14a produced by the mask 40, and is substantially free of any spurious reflections 14b. The filtered image 64 can then be evaluated using known algorithms to determine the depth of the focus of laser beam 14.

The invention claimed is:

1. Ophthalmological laser apparatus, wherein an interface device is coupleable to the laser apparatus and has an applanation element comprising a front surface and a back surface, wherein the laser apparatus comprises:
    optics that are adapted to focus the laser beam, which has a predefined shape, through the applanation element at a focus point,
    a detection element that is adapted to detect a superimposed image of a spurious reflection, which is reflected from the front surface, with a standard reflection, which is reflected from the back surface, and
    a processor that is adapted to numerically filter out the spurious reflection from the superimposed image, and determine a depth of the focus point of the laser beam based on the remaining standard reflection.

2. Ophthalmological laser apparatus according to claim 1, wherein the laser apparatus further comprises a mask for covering at least a portion of the laser beam, and wherein the optics are adapted to focus the laser beam through the mask so as to produce the predefined shape.

3. Ophthalmological laser apparatus according to claim 1, wherein the processor for filtering the spurious reflection is adapted to:
- convolute the superimposed image with a predefined reference pattern to produce an auxiliary image,
- evaluate the auxiliary image to identify a maximum point having a highest intensity,
- reposition the reference pattern based on a location of the maximum point, and
- multiply the superimposed image with the repositioned reference pattern to produce the standard reflection.

4. Ophthalmological laser apparatus according to claim 3, wherein the reference pattern comprises a centre point, and wherein the processor is adapted to reposition the reference pattern such that the centre point and the location of the maximum point are superimposed.

5. Ophthalmological laser apparatus according to claim 3, wherein the convolution of the superimposed image with the reference pattern is performed as a multiplication in the frequency domain.

6. Ophthalmological laser apparatus according to claim 3, wherein the processor is adapted to:
- apply a Fourier-transform to the superimposed image,
- multiply the Fourier-transformed superimposed image with a Fourier-transform of the reference pattern to produce a transformed auxiliary image, and
- perform a reverse-Fourier-transform on the transformed auxiliary image to produce the auxiliary image.

7. Ophthalmological laser apparatus according to claim 1, wherein the applanation element is free from a reflection-minimizing coating.

8. Ophthalmological laser apparatus according to claim 1, wherein the back surface of the applanation element is adapted to lie in contact with an eye that is to be examined.

9. Laser system with the ophthalmological laser apparatus according to one of the previous claims, and with an interface device which is coupleable to the laser apparatus and has an applanation element which is transparent or/and translucent to a laser beam produced by the laser apparatus, the applanation element comprising a front surface and a back surface.

10. Method to determine a depth of a focus point of a laser beam provided by an ophthalmological laser apparatus, the method comprising the following steps:
- focusing a laser beam, which has a predefined shape, through an applanation element at a focus, wherein the applanation element has a front surface and a back surface;
- detecting a superimposed image of a spurious reflection, which is reflected from the front surface, with a standard reflection, which is reflected from the back surface;
- numerically filtering out the spurious reflection from the superimposed image; and
- determining a depth of the focus point of the laser beam based on the remaining standard reflection.

11. Method according to claim 10, wherein the step of filtering out the spurious reflection comprises:
- convoluting the superimposed image with a predefined reference pattern, to produce an auxiliary image,
- evaluating the auxiliary image, to identify a maximum point having a highest intensity,
- repositioning the reference pattern based on a location of the maximum point, and
- multiplying the superimposed image with the repositioned reference pattern, to produce the standard reflection.

12. Method according to claim 11, wherein the step of convoluting comprises:
- applying a Fourier-transform to the superimposed image,
- multiplying the Fourier-transformed superimposed image with a Fourier-transform of the reference pattern, to produce a transformed auxiliary image, and
- performing a reverse-Fourier-transform on the transformed auxiliary image to produce the auxiliary image.

13. A non-transitory computer readable medium encoded with software, the software operable when executed to perform the following steps:
- focusing a laser beam, which has a predefined shape, through an applanation element at a focus, wherein the applanation element has a front surface and a back surface;
- detecting a superimposed image of a spurious reflection, which is reflected from the front surface, with a standard reflection, which is reflected from the back surface;
- numerically filtering out the spurious reflection from the superimposed image; and
- determining a depth of the focus point of the laser beam based on the remaining standard reflection.

* * * * *